(12) United States Patent
Khan

(10) Patent No.: US 7,514,579 B2
(45) Date of Patent: Apr. 7, 2009

(54) BORONIC CHALCONE DERIVATIVES AND USES THEREOF

(75) Inventor: Saeed R. Khan, Owings Mills, MD (US)

(73) Assignees: Johns Hopkins University, Baltimore, MD (US); Johns Hopkins Technology Transfer, Baltimore, MD (US)

( * ) Notice: Subject to any disclaimer, the term of this patent is extended or adjusted under 35 U.S.C. 154(b) by 392 days.

(21) Appl. No.: 10/517,781

(22) PCT Filed: Jun. 12, 2003

(86) PCT No.: PCT/US03/18962

§ 371 (c)(1),
(2), (4) Date: Apr. 20, 2005

(87) PCT Pub. No.: WO03/106384

PCT Pub. Date: Dec. 24, 2003

(65) Prior Publication Data

US 2005/0176988 A1 Aug. 11, 2005

Related U.S. Application Data

(60) Provisional application No. 60/444,429, filed on Feb. 3, 2003, provisional application No. 60/388,255, filed on Jun. 13, 2002.

(51) Int. Cl.
*C07F 5/02* (2006.01)
(52) U.S. Cl. .......................................................... 562/7
(58) Field of Classification Search ...................... 562/7
See application file for complete search history.

(56) References Cited

U.S. PATENT DOCUMENTS

| | | | |
|---|---|---|---|
| 5,808,137 A | 9/1998 | Bombardelli et al. |
| 5,814,622 A | 9/1998 | de Nanteuil et al. |
| 6,083,903 A | 7/2000 | Adams et al. |
| 6,147,082 A | 11/2000 | Bombardelli et al. |
| 6,297,217 B1 | 10/2001 | Adams et al. |
| 6,423,740 B1 | 7/2002 | Bombardelli et al. |
| 6,462,075 B1 | 10/2002 | Bowen et al. |

FOREIGN PATENT DOCUMENTS

WO 96/19209 A1 6/1996

OTHER PUBLICATIONS

DiCesare et al., Chalcone-analogue fluorescent probes for saccharides signaling using the boronic acid group, Tetrahedron Letters (2002), 43(14), 2615-2618.*
Baker et al., Suppression of human colorectal carcinoma cell growth by wild-type p53, Science, 1990, 249:912-5.
Bodor, Nicholas, Targeting of drugs to the brain, Methods in Enzymology, 112:381-96, 1985.
Boyd et al., A novel cellular protein (MTBP) binds to MDM2 and induces a $G_1$ arrest that is suppressed by MDM2, J. Biol. Chem., 2000, 275(41):31883-90.
Bundgaard, H., Means to enhance penetration, prodrugs as a means to improve the delivery of peptide drugs, Advanced Drug Delivery Reviews, 8:1-38, 1992.
Bundgaard, Hans, Formation of prodrugs of amines, amides, ureides, and imides, Methods in Enzymology, 112:347-59, 1985.
Calliste et al., Chalcones: structural requirements for antioxidant, estrogenic and antiproliferative activities, Anticancer Res., 2001, 21:3949-56.
De Vincenzo et al., Effect of synthetic and naturally occurring chalcones on ovarian cancer cell growth: structure-activity relationships, Anticancer Drug Des., 1995, 10:481-90.
Dicesare et al., Chalcone-analogue fluorescent prfobes for saccharides signaling using the boronic acid group, Tetrahedron Letters 43:2615-8, 2002.
Dicesare et al., New sensitive and selective fluorescent probes for fluoride using boronic acids, Analytical Biochemistry 301:111-6, 2002.
Diller et al., p53 Functions as a cell cycle control protein in osteosarcomas, Mol. Cell. Biol., 1990, 10(11):5772-81.
Fakharzadeh et al., Tumorigenic potential associated with enhanced expression of a gene that is amplified in a mouse tumor cell line, EMBO J., 1991, 10(6):1565-9.
Fleisher et al., Design of prodrugs for improved gastrointestinal absorption by intestinal enzyme targeting, Methods in Enzymology, 112:360-81, 1985.
Juven-Gershon et al., MDM2: The ups and downs, Mol. Med. 1999, 5:71-83.
Kakeya et al., Studies of prodrugs of cephalosporins. I. [1)] Synthesis and biological properties of glycyloxybenzoyloxymethyl and glycylaminobenzoyloxymethyl esters of 7β-[2-(2-aminothiazol-4-yl)-(Z)-2-methoxyiminoacetamido]-3-methyl-3-cephem-4-carboxylic acid, Chem. Pharm. Bull. 32:692-8, 1984.
Krogsgaard-Larsen et al., Design and application of prodrug, A Textbook of Drug Design and Development, edited by Krogsgaard-Larsen and H. Bundgaard, Chap. 5:113-91, 1991.

(Continued)

*Primary Examiner*—Daniel M Sullivan
*Assistant Examiner*—Chukwuma O Nwaonicha
(74) *Attorney, Agent, or Firm*—DLA Piper LLP (US)

(57) ABSTRACT

The present invention relates to novel boronic chalcone derivatives which are useful as antitumor/anticancer agents. The present compounds, which are inexpensive to synthesize, exhibit unexpectedly good inhibitors of the growth of human breast cancer cells. The present invention also relates to the use of the novel boronic chalcone derivatives to treat cancer. The invention also provides pharmaceutical compositions comprising the inhibitors of the invention and methods of utilizing the inhibitors and pharmaceutical compositions in the treatment and prevention of cancer.

10 Claims, 4 Drawing Sheets

OTHER PUBLICATIONS

Kumar et al., Design, Synthesis and evaluation of novel boronic-chalcone derivatives as antitumor agents, J. of Med. Chem., 46:2813-5, 2003.

Lane et al., MDM2-arbiter of p53's destruction, Trends Biochem. Sci., 1997, 22:372-4.

Lozano et al., MDM2 function, Biochem. Biophys. Acta, 1998, 1377:M55-M59.

Lundgren et al., Targeted expression of MDM2 uncouples S phase from mitosis and inhibits mammary gland development independent of p53, Genes Dev., 1997, 11:714-25.

Maggiolini et al., Estrogenic and antiproliferative activities of isoliquiritigenin in MCF7 breast cancer cells, J. Steroid Biochem. Mol. Biol. 2002, 82:315-22.

Makita et al., Chemoprevention of 4-nitroquinoline 1-oxide-induced rat oral carcinogenesis by the dietary flavonoids chalcone, 2-hydroxychalcone, and quercetin[1], Cancer Res., 1996, 56:4904-9.

Momand et al., The MDM2 gene amplification database, Nucleic Acids Res., 1998, 26(15):3453-9.

Mosmann, T., Rapid colorimetric assay for cellular growth and survival: application to proliferation and cytotoxicity assays, J. Immunol. Methods, 1983, 65:55-63.

Nelson, Sidney D., Alteration of drug metabolism by the use of prodrugs, Methods in Enzymology, 112:340-7, 1985.

Nielsen et al., Glycolamide esters as biolabile prodrugs of carboxylic acid agents: synthesis, stability, bioconversion, and physicochemical properties, Journal of Pharmaceutical Sciences, 77(4):285-98, 1988.

Notari, Robert E., Theory and Practice of prodrug kinetics, Methods in Enzymology, 112:309-23, 1985.

Oliner et al., Amplification of a gene encoding a p53-associated protein in human sarcomas, Nature, 1992, 358:80-3.

Rui, H., Research and development of cancer chemopreventive agents in China, J. Cell. Biochem. Supp., 1997, 27:7-11.

Satomi, Y., Inhibitory effects of 3'-methyl-3-hydroxy-chalcone on proliferation of human malignant tumor cells and on skin carcinogenesis, Int. J. Cancer, 1993, 55:506-14.

Schilsky et al., Infertility and carcinogenesis: late complications of chemotherapy, in Cancer Chemotherapy Principal and Practice, Chabner et al., Chapter 3:32-58, Lippincott Williams & Wilkins Publishers: Philadelphia, 1990.

Stoll et al., Chalcone derivatives antagonize interactions between the human oncoprotein MDM2 and p53, Biochemistry, 2001, 40:336-44.

Swain et al., Endocrine therapies of cancer, in Cancer Chemotherapy Principal and Practice, Chabner et al., Chapter 4:59-109, Lippincott Williams & Wilkins Publishers: Philadelphia, 1990.

Wang et al., Antisense anti-MDM2 oligonucleotides as a novel therapeutic approach to human breast cancer: in vitro and in vivo activities and mechanisms[1], Clinical Cancer Res., 2001, 7:3613-24.

Wasylyk et al., p53 mediated death of cells overexpressing MDM2 by an inhibitor of MDM2 interaction with p53, Oncogene, 1999, 18:1921-34.

Wattenberg et al., Inhibition of carcinogen-induced pulmonary and mammary carcinogenesis by chalcone administered subsequent to carcinogen exposure, Cancer Lett., 1994, 83:165-9.

Yamamoto et al., The potent anti-tumor-promoting agent isoliquiritigenin, Carcinogenesis, 1991, 12(2):317-23.

Zhang et al., MDM2 oncogene as a novel target for human cancer therapy, Curr. Pharm. Des., 2000, 6:393-416.

* cited by examiner

BORONIC CHALCONE DERIVATIVES AND USES THEREOF

RELATED APPLICATIONS

The present application claims priority of U.S. Provisional Patent Application No. 60/388,255 filed Jun. 13, 2002, and U.S. Provisional Patent Application No. 60/444,429 filed Feb. 3, 2003, both of which are incorporated herein in their entirety by this reference.

BACKGROUND OF THE INVENTION

1. Field of the Invention

This invention relates to novel boronic chalcone compounds and uses thereof. The compounds of this invention are particularly useful for the treatment of tumors and cancers.

2. Description of the State of the Art

Throughout this application, various publications are referenced by author and date. Full citations for these publications may be found listed at the end of the specification immediately preceding the claims. The disclosures of these publications are hereby incorporated by reference in their entireties into this application in order to more fully describe the state of the art as known to those skilled therein as of the date of this invention described and claimed herein.

Breast cancer is expected to account for 203,500 new cancer cases and 39,600 deaths in 2002 (Jemal, A. et al., *CA Cancer J. Clin.,* 2002, 52, 23-47). Although major advances have been made in early detection, prevention, and treatment, the need for more effective therapy in the fight against late stage breast cancer continues. Currently there is no curative treatment for women with metastatic breast cancer once they have failed adjuvant therapies. New and effective cytotoxic agents with novel mechanisms of action are therefore urgently needed for the treatment of women with metastatic breast cancer. Hormone and chemotherapy, while of substantial palliative benefit, has had little impact on overall survival and the mortality rate from metastatic breast cancer. At the present time standard treatments for metastatic breast cancer include paclitaxel in combination with vinca alkaloids, etoposide, and other regimens that include agents such as anthacyclines, alkylating agents, antimetabolites, tamoxifen, and aromatase inhibitors (Chabner B A, Collins J M, Cancer chemotherapy principal and practice, pp 9-13, and 40-85. B. Lippincott Company, Philadelphia, 1990). The ultimate conclusion of these numerous studies over the last 50 years is that although these therapies provides significant palliative effect in the majority of with metastatic breast patients, it is likely to be curative. Although major advances have been made in early detection, prevention, and treatment of early disease, the need for more effective therapy in the fight against late stage breast cancer continues.

Recently the mouse double minute 2 (MDM2) oncogene has been suggested as a target for breast cancer therapy (Juven-Gershon, T. and Oren, M. *Mol. Med.,* 1999, 5, 71-83; Momand, J. et al., *Nucleic Acids Res.,* 1998, 26, 3453-3459). MDM2 is amplified or overexpressed in human breast cancer, and MDM2 levels are associated with poor prognosis of human breast cancer. The oncoprotein MDM2 inhibits the tumor suppressor protein p53 by binding to the p53 transactivation domain. The p53 gene is inactivated in human cancer either by mutations or by binding to oncogenic proteins such as MDM2 (Lane, D. P. and Hall, P. A., *Trends Biochem. Sci.* 1997, 22, 372-374; Oliner, J. D. et al., *Nature,* 1992, 358, 80-83; Lozano, G.; Montes de Oca Luna, R., *Biochim. Biophys. Acta,* 1998, 1377, M55-M59; Wang, H. et al.; *Clinical Cancer Res.,* 2001, 7, 3613-3624). In breast tumors, over expression of MDM2 inactivates an otherwise intact p53, disabling the genome integrity checkpoint and allowing cell cycle progression of defective cells (Boyd, M. T. et al., *J. Biol. Chem.,* 2000, 275, 31883-31890). Studies comparing MDM2 overexpression and p53 mutation concluded that these are mutually exclusive events, supporting the notion that the primary impact of MDM2 amplification in cancer cells is the inactivation of the endogenous wild-type p53 (Wang et al., supra). It has been shown recently that a peptide homologue of p53 is sufficient to induce p53-dependent death of cells overexpressing MDM2 (Wasylyk, C., et al., *Oncogene,* 1999, 18, 1921-1934). This result provides clear evidence that disruption of the p53/MDM2 complex might be effective in cancer therapy. It has been shown that MDM2 additionally has a role in tumor growth p53-independent mechanisms (Baker, S. J., et al., *Science,* 1990, 249, 912-915; Diller, L., et al., *Mol. Cell. Biol.,* 1990, 10, 5772-5781; Fakharzadeh, S. S., et al., *EMBO J.,* 1991, 10, 1565; Lundgren, K.; Montes de Oca Luna, R., et al., *Genes Dev.,* 1997, 11, 714-725; Zhang, R. and Wang, H., *Curr. Pharm. Des.,* 2000, 6, 393-416; Chabner, B. A. and Collins, J. M., *Cancer chemotherapy principal and practice;* Lippincott Williams & Wilkins Publishers: Philadelphia, 1990; pp. 9-13 and 40-85B).

Chalcones are a class of anticancer agents that have shown promising therapeutic efficacy for the management of human cancers. Chalcones, considered as the precursor of flavonoids and isoflavonoids, are abundant in edible plants. Chemically they comprise open-chain flavonoids in which the two aromatic rings are joined by a three-carbon α,β-unsaturated carbonyl system. For example, chalcones have been observed to inhibit the proliferation of both established and primary ovarian cancer cells (De Vincenzo, R., et al., *Anticancer Drug Des.,* 1995, 10, 481-490). In vivo, chalcones have been demonstrated to be effective as antitumor agents in skin carcinogenesis (Statomi, Y., *Int. J. Cancer,* 1993, 55, 506-514; Yamamoto, S. et al., *Carcinogenesis,* 1991, 12, 317-323) and chemopreventive agents in several experimental models (Makita, H., et al., *Cancer Res.,* 1996, 56, 4904-4909; Rui, H., *J. Cell. Biochem.,* 1997, 67, 7-11; Wattenberg, L. W., et al., *Cancer Lett.,* 1994, 83, 165-169). Recent studies have shown that these chalcones induce apoptosis in variety of cell types including breast cancers (Claude-Alain, C., et al., *Anticancer Res.,* 2001, 21, 3949-3956; WO 01/117988; WO 96/19209; U.S. Pat. No. 5,808,137; Maggiolini, M., et al., *J. Steroid Biochem. Mol. Biol.,* 2002, 82, 315-322; Stoll, R., et al., *Biochemistry,* 2001, 40, 336-344; DiCesare, N. and Lakowicz, J. R., *Tetrahedron. Lett.,* 2002, 43, 2615-2618). Biochemical experiments have shown that these compounds could disrupt the MDM2/p53 protein complex, releasing p53 from both the p53/MDM2 and DNA-bound p53/MDM2 complexes (Stoll et al., supra).

Carboxylic chalcones have shown promising therapeutic efficacy for he management of human cancers (Daskiewicz, J. B., et al., *Tetrahedron Lett.* 1999, 40, 7095-7098; Devincenzo, R., et al., *Anti-Cancer Drug Des.* 1995, 10, 481-490). Previous studies (Stoll et al., supra; Kussie, P. H., et al., *Science,* 1996, 274, 948-953) on the binding modes of carboxylic acid analogs of chalcones with MDM2 revealed that the carboxylic acid group could be placed near the base of lysine51 (K51), which is found in a salt bridge interaction with glutamic acid 25 (E25). It was presumed that the acid group of the chalcone forms a salt bridge with K51 and simultaneously breaks the salt bridge with E25 of the MDM2. However, carboxylic acid analogs of chalcone reported in the literature (Stoll et al., supra) are equally toxic to both normal and malignant breast epithelial cells. The toxicity to normal breast cells may be due to MDM2/p53 independent mechanisms. Therefore, a chalcone derivative that could strongly and irreversibly bind to and disrupt MDM2 protein complexes may be selectively toxic to MDM2 overexpressing breast cancer cells.

Boronic acids are Lewis acids and isosteres of carboxylic acid. The pKa's of boronic acids are about 9-10, and therefore at physiological pH boronic acids remain unionized (Tongcharoensirikul, P., et al., *Abstracts of Papers, 222$^{nd}$ ACS national meeting*, Chicago, Ill., August 26-30; American chemical society, Washington, DC, 2001; MEDI-224). Thus, a coordinate covalent bond (boron-nitrogen) can be formed between a electron deficient boronic acid moiety and electron-donating amino group, which may strongly enhance binding of boronic-chalcones with the lysine 51 of MDM2 at neutral pH when compared to the corresponding carboxylic acid analog of chalcones.

Boronic chalcone analogs have been previously described. These compounds have been used as fluorescent probes that may be useful for detection of fluorides (DiCesare, N. and Lakowicz, J. R., supra) and saccharides such as glucose that may be applicable to the design of biosensors for diabetes (DiCesare, N. and Lakowicz, J. R;, supra). However, prior to this invention no investigations into the anticancer activity of boronic-chalcones on different cancer cell lines have been reported.

SUMMARY OF THE INVENTION

Surprisingly, it has now been found that certain novel chalcones derivatives, in particular boronic chalcone derivatives, possess antiproliferative activity on cancer cells at micromolar concentrations. Accordingly, this invention provides the design and synthesis of novel boronic chalcone derivatives, and pharmaceutical compositions containing these compounds. Several the compounds described herein were observed to have high activity in the breast cancer cell lines tested and has been shown to be 6-9 fold less toxic to normal MCF-12A cell lines compared to normal breast epithelial cell lines. The novel boronic chalcone analogs disclosed herein should overcome the limiting lack of specificity of carboxylic acid analogs of chalcones.

The present invention further investigates the potential value of MDM2 as a drug target for breast cancer therapy. For example, a chalcone derivative of this invention that inhibits MDM2 expression or binds to and disrupts the MDM2 protein complex may be a useful compound for the treatment of breast cancer. While not wishing to be bound by any theory, it is believed that the boronic acid analog might form a stronger salt bridge with K51 of MDM2 than the corresponding carboxylic acid analogs of chalcones and will selectively inhibit growth of breast cancer cells. Accordingly, a set of boronic acid-chalcone derivatives were designed and tested their ability to selectively kill breast cancer over normal breast epithelial cells.

In general, one embodiment of the invention relates to boronic-chalcone compounds of the general Formula I:

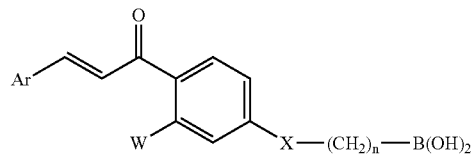

where

Ar is aryl or heteroaryl, each of which may be substituted or unsubstituted;

W is H, $Z_n$-F, $Z_n$-Cl, $Z_n$-Br, $Z_n$-I, $Z_n$-CF$_3$, $Z_n$-NO$_2$, $Z_n$-OR$^1$, $Z_n$-NR$^1$R$^2$, $Z_n$-COOR$^1$, $Z_n$-SR$^1$, $Z_n$-(C=O)R$^1$, $Z_n$-O(C=O)R$^1$, $Z_n$-NR$^1$(C=O)R$^1$, $Z_n$-(C=O)NR$^1$, alkyl, allyl, alkenyl, alkynyl, heteroalkyl, heteroallyl, heteroalkenyl, heteroalkynyl, alkoxy, heteroalkoxy, $Z_n$-cycloalkyl, $Z_n$-heterocycloalkyl, $Z_n$-Ar or $Z_n$-heteroaryl, wherein said alkyl, allyl, alkenyl, alkynyl, heteroalkyl, heteroallyl, heteroalkenyl, heteroalkynyl, alkoxy, heteroalkoxy, $Z_n$-cycloalkyl, $Z_n$-heterocycloalkyl, $Z_n$-Ar or $Z_n$-heteroaryl may be substituted or unsubstituted;

X is $Z_n$, $Z_n$-O, $Z_n$-S, $Z_n$-NR$^1$, $Z_n$-NR$^1$(C=O), $Z_n$-C=O, $Z_n$-OC(=O), or $Z_n$-C(=O)O;

R$^1$ and R$^2$ are independently H, an amine protecting group, an alcohol protecting group, an acid protecting group, a sulfur protecting group, alkyl, allyl, alkenyl, alkynyl, heteroalkyl, heteroallyl, heteroalkenyl, heteroalkynyl, alkoxy, heteroalkoxy, $Z_n$-cycloalkyl, $Z_n$-heterocycloalkyl, $Z_n$-Ar or $Z_n$-heteroaryl, wherein said alkyl, allyl, alkenyl, alkynyl, heteroalkyl, heteroallyl, heteroalkenyl, heteroalkynyl, alkoxy, heteroalkoxy, $Z_n$-cycloalkyl, $Z_n$-heterocycloalkyl, $Z_n$-Ar or $Z_n$-heteroaryl may be substituted or unsubstituted, or R$^1$ together with R$^2$ and N forms a saturated or partially unsaturated heterocycle ring having 1 or more heteroatoms in said ring, wherein said heterocycle may be substituted or unsubstituted and wherein said heterocycle may be fused to an aromatic ring;

Z is an alkylene having at least 1 carbon, or an alkenylene or alkynylene each having at least 2 carbons, wherein said alkylene, alkenylene, or alkynylene may be substituted or unsubstituted; and n is zero or any integer.

The invention is also directed to pharmaceutically acceptable prodrugs, pharmaceutically active metabolites, and pharmaceutically acceptable salts of the compound of Formula I. Methods of making the compounds of Formula I are also described.

In another embodiment, this invention relates to compounds of the general Formula II:

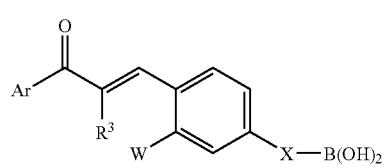

where Ar, W, X and n are as defined above and R$^3$ is an electron-withdrawing moiety. The invention is also directed to pharmaceutically acceptable prodrugs, pharmaceutically active metabolites, and pharmaceutically acceptable salts of the compound of Formula II. Methods of making the compounds of Formula II are also described.

In another embodiment, this invention relates to compounds of the general Formula III:

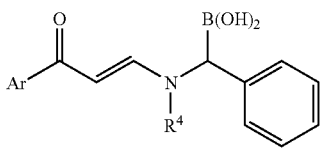

III where Ar is as defined above and $R^4$ is H, an amine protecting group, $Z_n$-$OR^1$, $Z_n$-$SR^1$, $Z_n$-$NR^1$, $Z_n$-$NR^1(C=O)R^1$, $Z_n$-$C=OR^1$, $Z_n$-$OC(=O)R^1$, $Z_n$-$C(=O)OR^1$, alkyl, allyl, alkenyl, alkynyl, heteroalkyl, heteroallyl, heteroalkenyl, heteroalkynyl, alkoxy, heteroalkoxy, $Z_n$-cycloalkyl, $Z_n$-heterocycloalkyl, $Z_n$-Ar or $Z_n$-heteroaryl, wherein said alkyl, allyl, alkenyl, alkynyl, heteroalkyl, heteroallyl, heteroalkenyl, heteroalkynyl, alkoxy, heteroalkoxy, $Z_n$-cycloalkyl, $Z_n$-heterocycloalkyl, $Z_n$-Ar or $Z_n$-heteroaryl may be substituted or unsubstituted, and where $Z_n$, $R^1$ and n are as defined above. The invention is also directed to pharmaceutically acceptable prodrugs, pharmaceutically active metabolites, and pharmaceutically acceptable salts of the compound of Formula III. Methods of making the compounds of Formula III are also described.

The invention further relates to a method for treating proliferative diseases such as cancers. More specifically, one embodiment of this invention provides a method of treating or preventing a tumor or cancer in a patient comprising administering to said patient in need thereof an effective amount of a compound having the Formula I-III or a pharmaceutically-acceptable salt or in vivo cleavable prodrug thereof. Other aspects of the invention include methods for treating cancers mediated by MDM2. Examples of cancers that may be treated of prevented by the compounds of this invention include, but are not limited to, breast, colorectal, cervical, ovarian, brain, acute leukemia, gastric, non-small cell lung, pancreatic, and renal cancer.

The invention also features methods of combination therapy, such as a method for treating cancer, wherein the above methods further include providing radiation therapy or chemotherapy. The chemotherapy or radiation therapy may be administered before, concurrently, or after the administration of a disclosed compound according to the needs of the patient.

In a further aspect the present invention provides methods of inhibiting MDM2 expression in a mammal, comprising administering an amount of a compound effective to inhibit said expression, said compound having the Formula I-III or a pharmaceutically acceptable salt or in vivo cleavable prodrug thereof.

The invention also relates to pharmaceutical compositions comprising an effective amount of an agent selected from compounds of Formulas I-III or a pharmaceutically acceptable prodrug, pharmaceutically active metabolite, or pharmaceutically acceptable salt thereof.

Additional advantages and novel features of this invention shall be set forth in part in the description that follows, and in part will become apparent to those skilled in the art upon examination of the following specification or may be learned by the practice of the invention. The advantages of the invention may be realized and attained by means of the instrumentalities, combinations, compositions, and methods particularly pointed out in the appended claims.

BRIEF DESCRIPTION OF THE FIGURES

The accompanying drawings, which are incorporated herein and form a part of the specification, illustrate non-limiting embodiments of the present invention, and together with the description, serve to explain the principles of the invention.

In the Figures.

DETAILED DESCRIPTION OF THE INVENTION

Figure 1:
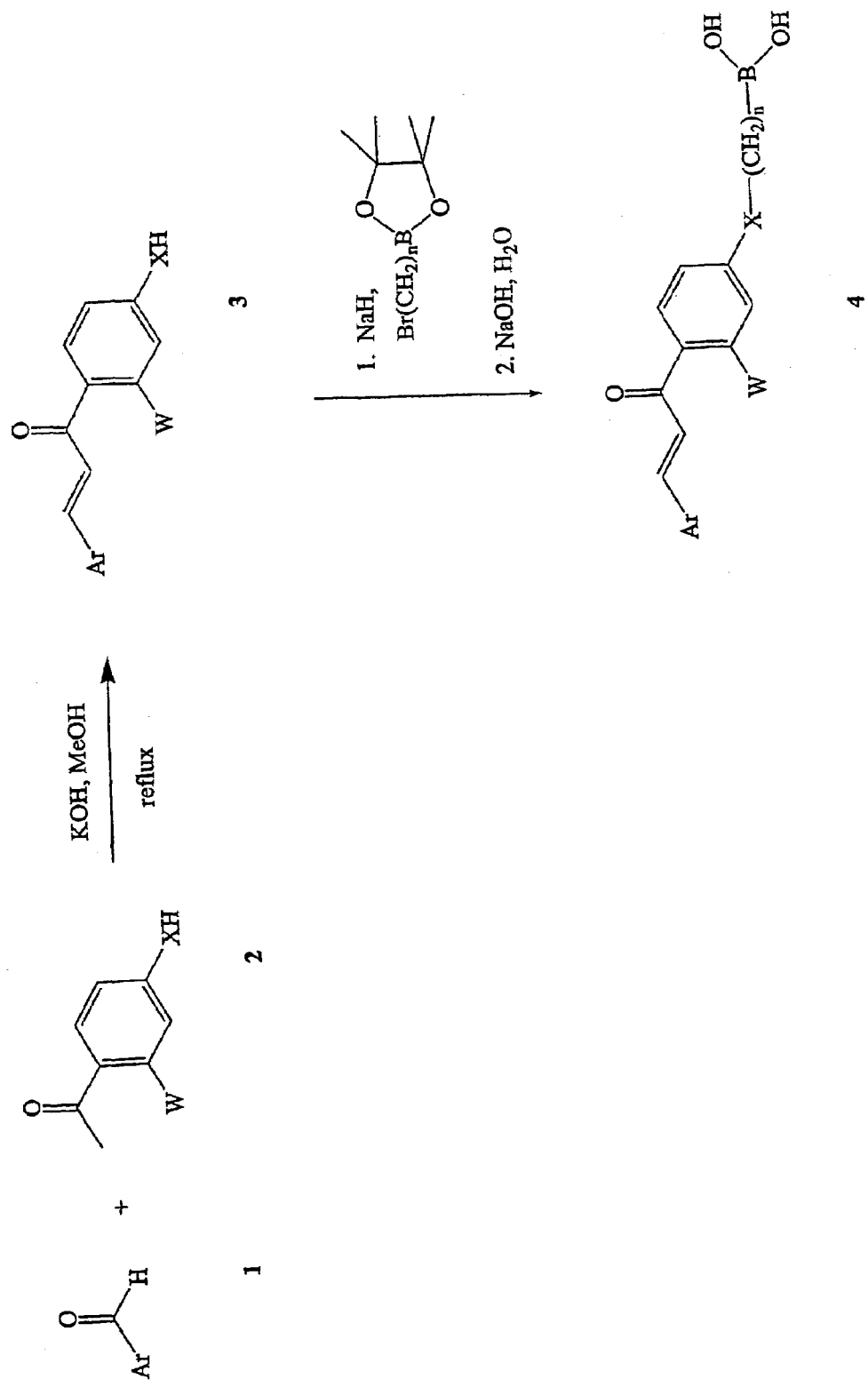
FIG. 1 shows a reaction scheme for the synthesis of compound 4.

The invention features novel boronic chalcone compounds having Formulas I-III, pharmaceutical compositions thereof, and methods of using such compounds and compositions. The inventive compounds of the Formulas I-III are useful, for example, for treating a tumor or cancer in a patient. Such compounds have particular utility as therapeutic agents for diseases that can be treated by the inhibition of MDM2 expression.

The term "tumor" as used herein refers to abnormal growth in tissue which occurs when cellular proliferation is more rapid than normal tissue and continues to grow after the stimuli that initiated the new growth cease. Tumors generally exhibit partial or complete lack of structural organization and functional coordination with the normal tissue, and usually form a distinct mass of tissue which may be benign (benign tumor) or malignant (carcinoma). Tumors tend to be highly vascularized.

The term "cancer" is used as a general term herein to describe malignant tumors or carcinoma. These malignant tumors may invade surrounding tissues, may metastasize to several sites and are likely to recur after attempted removal and to cause death of the patient unless adequately treated. As used herein, the terms carcinoma and cancer are subsumed under the term tumor.

In general, one embodiment of the invention relates to novel boronic chalcone compounds of the general Formula I:

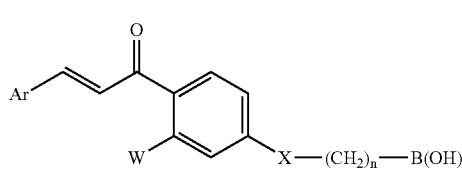

I where
Ar is aryl or heteroaryl, each of which may be substituted or unsubstituted;
W is H, $Z_n$-F, $Z_n$-Cl, $Z_n$-Br, $Z_n$-I, $Z_n$-$CF_3$, $Z_n$-$NO_2$, $Z_n$-$OR^1$, $Z_n$-$NR^1R^2$, $Z_n$-$COOR^1$, $Z_n$-$SR^1$, $Z_n$-$(C=O)R^1$, $Z_n$-$O(C=O)R^1$, $Z_n$-$NR^1(C=O)R^1$, $Z_n$-$(C=O)NR^1$, alkyl, allyl, alkenyl, alkynyl, heteroalkyl, heteroallyl, heteroalkenyl, heteroalkynyl, alkoxy, heteroalkoxy, $Z_n$-cycloalkyl, $Z_n$-heterocycloalkyl, $Z_n$-Ar or $Z_n$-heteroaryl, wherein said alkyl, allyl, alkenyl, alkynyl, heteroalkyl, heteroallyl, heteroalkenyl, heteroalkynyl, alkoxy, heteroalkoxy, $Z_n$-cycloalkyl, $Z_n$-heterocycloalkyl, $Z_n$-Ar or $Z_n$-heteroaryl may be substituted or unsubstituted;

X is $Z_n$, $Z_n$-O, $Z_n$-S, $Z_n$-NR$^1$, $Z_n$-NR$^1$(C=O), $Z_n$-C=O, $Z_n$-OC(=O), or $Z_n$-C(=O)O;

$R^1$ and $R^2$ are independently H, an amine protecting group, an alcohol protecting group, an acid protecting group, a sulfur protecting group, alkyl, allyl, alkenyl, alkynyl, heteroalkyl, heteroallyl, heteroalkenyl, heteroalkynyl, alkoxy, heteroalkoxy, $Z_n$-cycloalkyl, $Z_n$-heterocycloalkyl, $Z_n$-Ar or $Z_n$-heteroaryl, wherein said alkyl, allyl, alkenyl, alkynyl, heteroalkyl, heteroallyl, heteroalkenyl, heteroalkynyl, alkoxy, heteroalkoxy, $Z_n$-cycloalkyl, $Z_n$-heterocycloalkyl, $Z_n$-Ar or $Z_n$-heteroaryl may be substituted or unsubstituted, or $R^1$ together with $R^2$ and N forms a saturated or partially unsaturated heterocycle ring having 1 or more heteroatoms in said ring, wherein said heterocycle may be substituted or unsubstituted and wherein said heterocycle may be fused to an aromatic ring;

Z is an alkylene having at least 1 carbon, or an alkenylene or alkynylene each having at least 2 carbons, wherein said alkylene, alkenylene, or alkynylene may be substituted or unsubstituted; and n is zero or any integer.

The term "aryl" means a monovalent aromatic hydrocarbon monocyclic radical of 6 to 10 ring atoms or a polycyclic aromatic hydrocarbon, optionally substituted independently with one or more substituents described herein. Examples of aryl groups include, but are not limited to, phenyl, 1-naphthyl, 2-naphthyl, and derivatives thereof.

The term "heteroaryl" means a monovalent monocyclic aromatic radical of 5 to 10 ring atoms or a polycyclic aromatic radical, containing one or more ring heteroatoms selected from N, O, or S, the remaining ring atoms being C. The aromatic radical is optionally substituted independently with one or more substituents described herein. Examples include, but are not limited to, furyl, thienyl, pyrrolyl, pyrazolyl, pyrimidinyl, imidazolyl, indolyl, quinolyl, benzopyranyl, thiazolyl, oxazolyl, isoxazolyl, thiophenyl, 1,3,4-triazolyl, tetrazolyl, pyridinyl, pyrimidinyl, pyridazinyl, indolyl, and derivatives thereof.

Alkyl groups include aliphatic (i.e., hydrocarbyl or hydrocarbon radical structures containing hydrogen and carbon atoms) with a free valence. Alkyl groups are understood to include straight chain and branched structures. The alkyl group can be substituted with one or more substituents which are independently selected from the substituents described herein. Examples of alkyl groups include, but are not limited to, methyl, ethyl, n-propyl, isopropyl, butyl, isobutyl, sec-butyl, tert-butyl, pentyl, isopentyl, tert-pentyl, hexyl, isohexyl, and the like.

Alkenyl groups are analogous to alkyl groups, but have at least one double bond (two adjacent sp$^2$ carbon atoms). Depending on the placement of a double bond and substituents, if any, the geometry of the double bond may be entgegen (E), or zusammen (Z), cis, or trans. Similarly, alkynyl groups are analogous to alkyl groups, but have at least one triple bond (two adjacent sp carbon atoms). Unsaturated alkenyl or alkynyl groups may have one or more double or triple bonds, respectively, or a mixture thereof; like alkyl groups, unsaturated groups may be straight chain or branched, and they may be substituted as described both above for alkyl groups and throughout the disclosure by example. The alkenyl or alkynyl groups can be substituted with one or more substituents which are independently selected from the substituents described herein.

The term "alkylene" means a linear or branched saturated divalent hydrocarbon radical of one to twelve carbon atoms, e.g., methylene, ethylene, propylene, 2-methylpropylene, pentylene, and the like.

The term "alkenylene" refers to a linear or branched divalent hydrocarbon radical of two to twelve carbons containing at least one double bond, wherein the alkenylene radical may be optionally substituted independently with one or more substituents described herein. Examples include, but are not limited to, ethenylene, propenylene, and the like.

The term "alkynylene" to a linear or branched divalent hydrocarbon radical of two to twelve carbons containing at least one triple bond, wherein the alkynylene radical may be optionally substituted independently with one or more substituents described herein.

The term "allyl" refers to a radical having the formula $R^1C$=CHCHR$^2$, wherein $R^1$ and $R^2$ are independently alkyl, alkenyl, alkynyl, cycloalkyl, heterocycloalkyl, aryl, heteroaryl, or any substituent as defined herein, wherein the allyl may be optionally substituted independently with one or more substituents described herein.

The term "cycloalkyl" refers to saturated or partially unsaturated cyclic hydrocarbon radical having from three to twelve carbon atoms, wherein the cycloalkyl may be optionally substituted independently with one or more substituents described herein. The term "cycloalkyl" further includes bicyclic and tricyclic cycloalkyl structures, wherein the bicyclic and tricyclic structures may include a saturated or partially unsaturated cycloalkyl fused to a saturated or partially unsaturated cycloalkyl or heterocycloalkyl ring or an aryl or heteroaryl ring. Examples of cycloalkyl groups include, but are not limited to, cyclopropyl, cyclobutyl, cyclopentyl, cyclohexyl, cycloheptyl, and the like.

The term "heteroalkyl" refers to saturated linear or branched-chain monovalent hydrocarbon radical of one to twelve carbon atoms, wherein at least one of the carbon atoms is replaced with a heteroatom selected from N, O, or S, and wherein the radical may be a carbon radical or heteroatom radical (i.e., the heteroatom may appear in the middle or at the end of the radical). The heteroalkyl radical may be optionally substituted independently with one or more substituents described herein. The term "heteroalkyl" encompasses alkoxy and heteroalkoxy radicals.

The term "heterocycloalkyl" refers to a saturated or partially unsaturated cyclic radical of 3 to 8 ring atoms in which at least one ring atom is a heteroatom selected from nitrogen, oxygen and sulfur, the remaining ring atoms being C where one or more ring atoms may be optionally substituted independently with one or more substituent described below. The radical may be a carbon radical or heteroatom radical. "Heterocycloalkyl" also includes radicals where heterocycle radicals are fused with aromatic or heteroaromatic rings. Examples of heterocycloalkyl rings include, but are not limited to, piperidyl, quinolyl, isothiazolyl, piperidinyl, morpholinyl, piperazinyl, tetrahydrofuryl, tetrahydropyrrolyl, pyrrolidinyl, octahydroindolyl, octahydrobenzothiofuranyl, and octahydrobenzofuranyl.

The term "heteroalkenyl" refers to linear or branched-chain monovalent hydrocarbon radical of two to twelve carbon atoms, containing at least one double bond, e.g., ethenyl, propenyl, and the like, wherein at least one of the carbon atoms is replaced with a heteroatom selected from N, O, or S, and wherein the radical may be a carbon radical or heteroatom radical (i.e., the heteroatom may appear in the middle or at the end of the radical). The heteroalkenyl radical may be optionally substituted independently with one or more substituents described herein, and includes radicals having "cis" and "trans" orientations, or alternatively, "E" and "Z" orientations.

The term "heteroalkynyl" refers to a linear or branched monovalent hydrocarbon radical of two to twelve carbon atoms containing at least one triple bond. Examples include, but are not limited to, ethynyl, propynyl, and the like, wherein at least one of the carbon atoms is replaced with a heteroatom selected from N, O, or S, and wherein the radical may be a carbon radical or heteroatom radical (i.e., the heteroatom may appear in the middle or at the end of the radical). The heteroalkynyl radical may be optionally substituted independently with one or more substituents described herein.

The term "heteroallyl" refers to radicals having the formula RC=CHCHR$^1$, wherein R and R$^1$ are independently alkyl, alkenyl, alkynyl, cycloalkyl, heterocycloalkyl, aryl, heteroaryl, or any substituent as defined herein, wherein at least one of the carbon atoms is replaced with a heteroatom selected from N, O, or S, and wherein the radical may be a carbon radical or heteroatom radical (i.e., the heteroatom may appear in the middle or at the end of the radical). The heteroallyl may be optionally substituted independently with one or more substituents described herein.

As used herein, the term "electron withdrawing moiety" is known in the art, and refers to a group which has a greater electron withdrawing effect than hydrogen. A variety of electron-withdrawing groups are known, and include halogens (e.g., fluoro, chloro, bromo, and iodo groups), $NO_2$, $NH_2$, CN, $SO_2R^1$, $SO_2Ar$, COOH, OAr, COOR$^1$, OR$^1$, COR$^1$, SH, SR$^1$, OH, $CF_3$, Ar, alkenyl, alkynyl or allyl, wherein said Ar, alkenyl, alkynyl and allyl may be optionally unsubstituted or substituted with an electron withdrawing moiety.

The term "amino protecting group" refers to those organic groups intended to protect nitrogen atoms against undesirable reactions during synthetic procedures and include, but are not limited to, benzyl, benzyloxycarbonyl (CBZ), tert-butoxycarbonyl (Boc), trifluoroacetyl, and the like.

The term "alcohol protecting group" refers to those organic groups intended to protect alcohol groups or substituents against undesirable reactions during synthetic procedures and include, but are not limited to, (trimethylsilyl)ethoxymethyl (SEM), tert-butyl, methoxymethyl (MOM), and the like.

The term "sulfur protecting groups" refers to those organic groups intended to protect sulfur groups or substituents against undesirable reactions during synthetic procedures and include, but are not limited to, benzyl, (trimethylsilyl) ethoxymethyl (SEM), tert-butyl, trityl and the like.

The term "acid protecting groups" refers to those organic groups intended to protect acid groups or substituents against undesirable reactions during synthetic procedures and include, but are not limited to, benzyl, (trimethylsilyl) ethoxymethyl (SEM), methylethyl and tert-butyl esters, and the like.

In general, the various moieties or functional groups of the compounds of Formulas I-III may be optionally substituted by one or more substituents. Examples of substituents suitable for purposes of this invention include, but are not limited to, F, Cl, Br, I, alkyl, allyl, alkenyl, alkynyl, heteroalkyl, heteroallyl, heteroalkenyl, heteroalkynyl, alkoxy, heteroalkoxy, $Z_n$-cycloalkyl, $Z_n$-heterocycloalkyl, $Z_n$-OR$^1$, $Z_n$-$NO_2$, $Z_n$-CN, $Z_n$-$CO_2R^1$, $Z_n$-(C=O)R$^1$, $Z_n$-O(C=O)R$^1$, $Z_n$-O-alkyl, $Z_n$-OAr, $Z_n$-SH, $Z_n$-SR$^1$, $Z_n$-SOR$^1$, $Z_n$-$SO_2R^1$, Zn—S—Ar, $Z_n$-SOAr, $Z_n$-$SO_2$Ar, $Z_n$-Ar, $Z_n$-heteroaryl, Zn—(C=O)NR$^1$R$^2$, $Z_n$-NR$^1$R$^2$, $Z_n$-NR$^1$(C=O)R$^1$, $Z_n$-$SO_2$NR$^1$R$^2$, $PO_3H_2$, $SO_3H_2$, amine protecting groups, alcohol protecting groups, sulfur protecting groups, or acid protecting groups, where:

Z is alkylene having from 1 to 4 carbons, or alkenylene or alkynylene each having from 2 to 4 carbons, wherein said alkylene, alkenylene, or alkynylene may be substituted or unsubstituted;

n is zero or any integer,

R$^1$ and R$^2$ are alkyl, allyl, alkenyl, alkynyl, heteroalkyl, heteroallyl, heteroalkenyl, heteroalkynyl, alkoxy, heteroalkoxy, $Z_n$-cycloalkyl, or $Z_n$-heterocycloalkyl, Ar or heteroaryl, wherein said alkyl, allyl, alkenyl; alkynyl, heteroalkyl, heteroallyl, heteroalkenyl, heteroalkynyl, alkoxy, heteroalkoxy, $Z_n$-cycloalkyl, $Z_n$-heterocycloalkyl, Ar, or heteroaryl may be substituted or unsubstituted.

The compounds of this invention may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. Accordingly, this invention also includes racemates and resolved enantiomers, and diastereomers compounds of the Formulas I-III. The methods for the determination of stereochemistry and the separation of stereoisomers are well known in the art (see discussion in Chapter 4 of "Advanced Organic Chemistry", 4th edition J. March, John Wiley and Sons, New York, 1992).

Certain of the compounds of this invention, in pharmaceutical dosage form, may be used as a method of treating a cancer or as a prophylactic agent for preventing a disease or condition from manifesting itself. Accordingly, this invention further includes compositions including, but not limited to, solvates, pharmaceutically acceptable prodrugs, pharmaceutically active metabolites, and pharmaceutically acceptable salts of compounds of Formulas I-III. The term "solvate" refers to an aggregate of a molecule with one or more solvent molecules.

In certain pharmaceutical dosage forms, the pro-drug form of the compounds according to the present invention may be preferred. A "prodrug" is a compound that may be converted under physiological conditions or by solvolysis to the specified compound or to a pharmaceutically acceptable salt of such compound.

A "pharmaceutically active metabolite" is a pharmacologically active product produced through metabolism in the body of a specified compound or salt thereof. Metabolites of a compound may be identified using routine techniques known in the art and their activities determined using tests such as those described herein.

Prodrugs and active metabolites of a compound may be identified using routine techniques known in the art. Various forms-of prodrugs are known in the art. For examples of such prodrug derivatives, see, for example, a) *Design of Prodrugs*, edited by H. Bundgaard, (Elsevier, 1985) and *Methods in Enzymology*, Vol. 42, p. 309-396, edited by K. Widder, et al. (Academic Press, 1985); b) *A Textbook of Drug Design and Development*, edited by Krogsgaard-Larsen and H. Bundgaard, Chapter 5 *"Design and Application of Prodrug"* (H. Bundgaard p. 113-191 (1991)); c) H. Bundgaard, *Advanced Drug Delivery Reviews,* 8, 1-38 (1992); d) H. Bundgaard, et al., *Journal of Pharmaceutical Sciences,* 77:285 (1988); and e) N. Kakeya, et al., *Chem. Pharm. Bull.,* 32: 692 (1984).

The compounds of this invention, including prodrug forms of these agents, can be provided in the form of pharmaceutically acceptable salts. As used herein, the term pharmaceutically acceptable salts or complexes refers to appropriate salts or complexes of the active compounds according to the present invention which retain the desired biological activity of the parent compound and exhibit limited toxicological effects to normal cells. Nonlimiting examples of such salts are acid addition salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, pamoic acid, alginic acid, and polyglutamic acid, among others The inventive compounds may be prepared using the reaction routes and synthesis schemes as described below, employing the techniques available in the art using starting materials that are readily available. For example, in one embodiment boronic chalcone compound (4), which is based upon a chemical structure I:

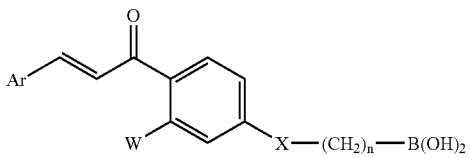

I can be prepared according to the reaction scheme shown in FIG. 1. In FIG. 1, aldehyde (1) and ketone (2) undergo a Claisen-Schmidt aldol condensation upon treatment with potassium hydroxide in methanol according to standard methods to provide compound (3). Treatment of compound (3) with pinacol(bromoalkyl)boronate in the presence of sodium hydride in THF followed by deprotection under alkaline conditions provides the desired compound (4).

In another embodiment, this invention relates to compounds of the general Formula II:

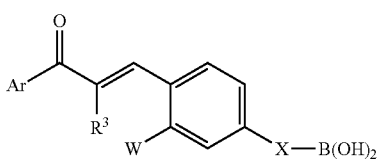

Figure 2:
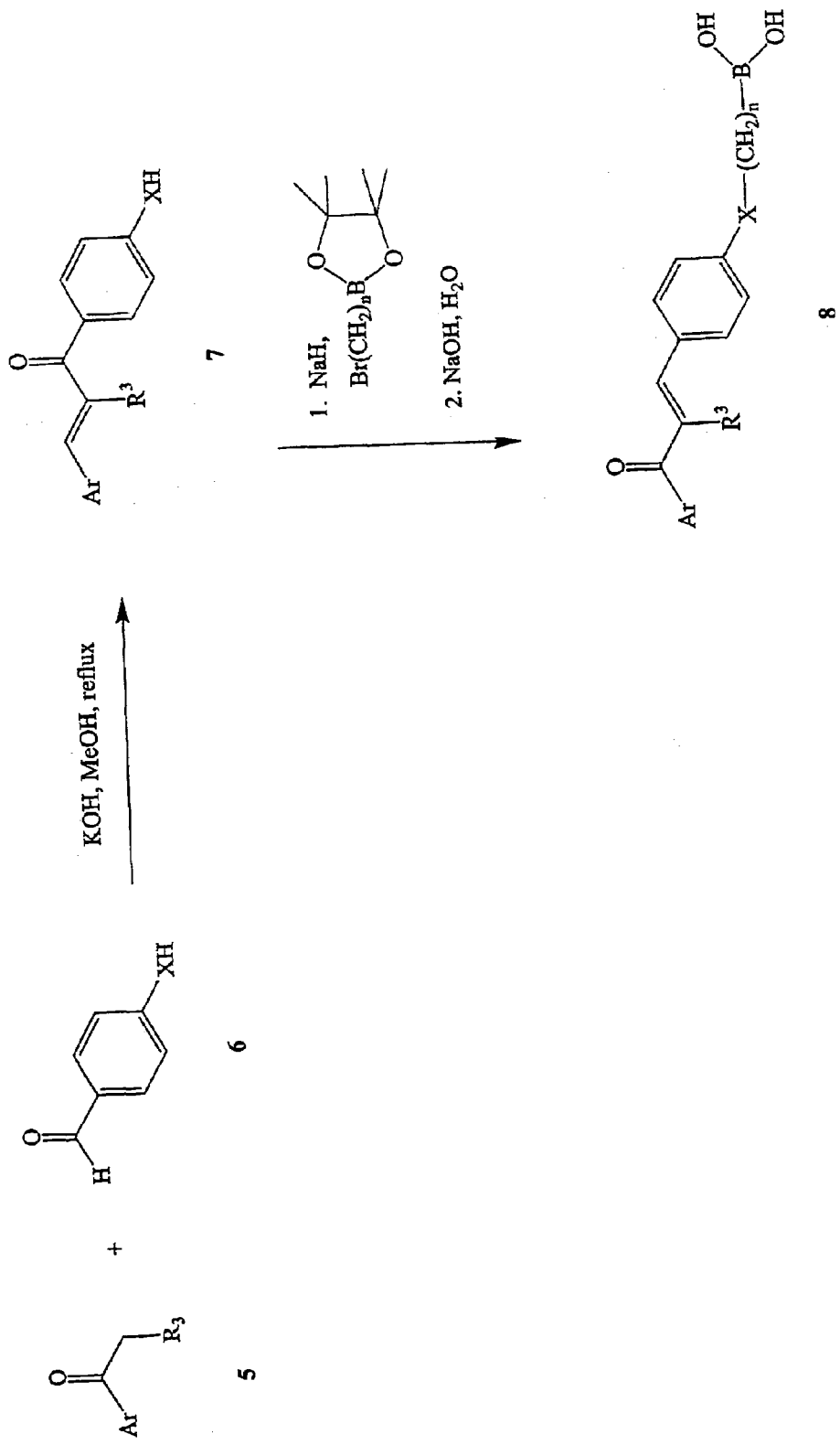
FIG. 2 shows a reaction scheme for the synthesis of compound 8.

II where Ar, W, X and n are as defined above and $R^3$ is an electron-withdrawing moiety. Boronic chalcone compound (8), which is based upon structure II can prepared according to the general reaction scheme shown in FIG. 2. In FIG. 2, ketone (5) and aldehyde (6) undergo a Claisen-Schmidt aldol condensation upon treatment with potassium hydroxide in methanol according to standard methods to provide compound (7). Treatment of compound (7) with pinacol(bromoalkyl)boronate in the presence of sodium hydride in THF, followed by deprotection under alkaline conditions provides the desired compound (8).

Figure 3:
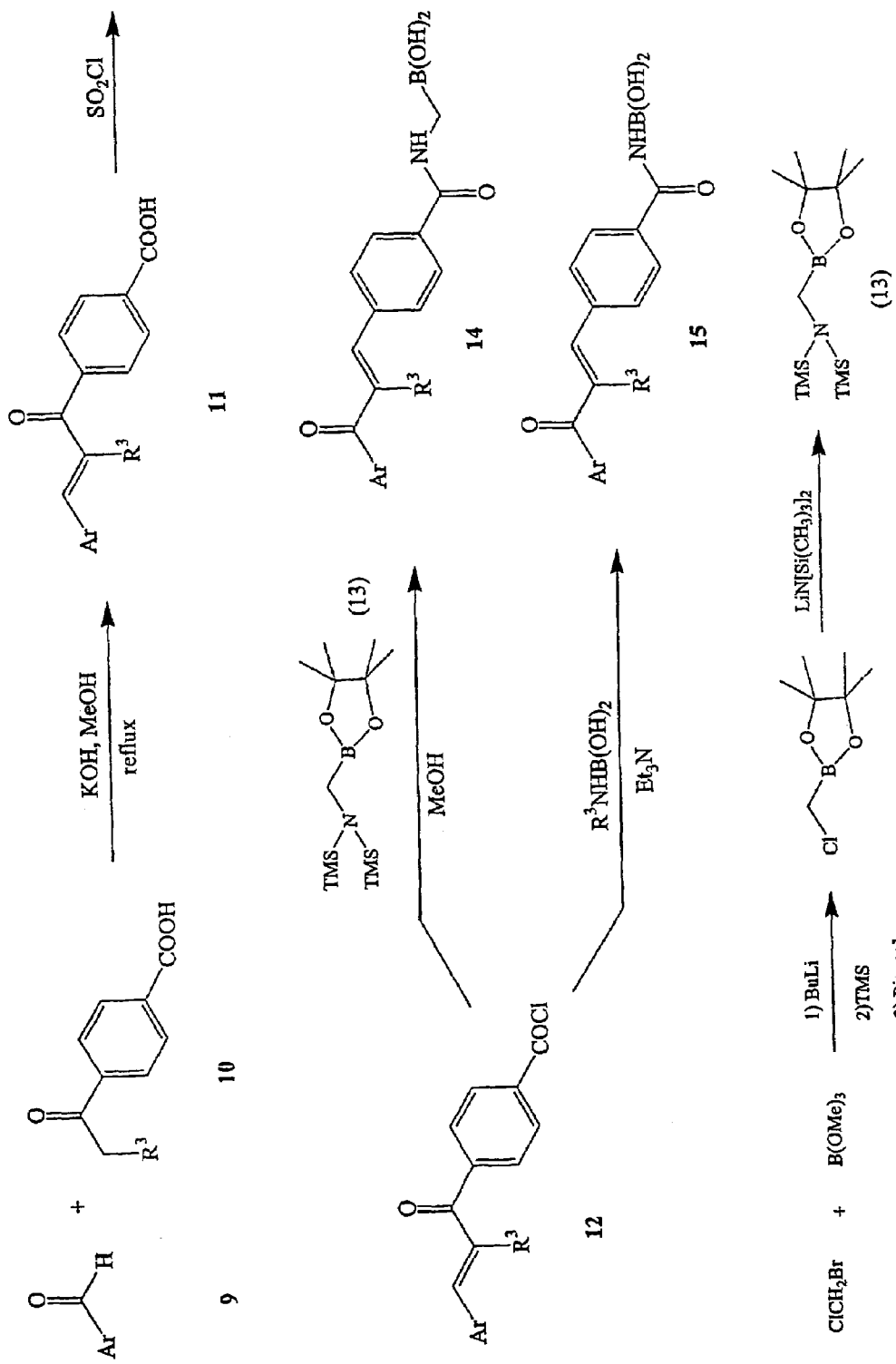
FIG. 3 shows a reaction scheme for the synthesis of compounds 14 and 15.

FIG. 3 shows another general reaction scheme for the syntheses of compounds (14) and (15), which are also based upon a chemical structure II. According to FIG. 3, aldehyde (9) and ketone (10) undergo a Claisen-Schmidt aldol condensation upon treatment with potassium hydroxide in methanol according to standard methods to provide compound (11). Compound (11) is converted to the acid chloride (12) by treating with thionyl chloride. Treatment of the acid chloride (12) with pinacol bis(trimethylsilyl)aminoalkylboronate (13) provides compound (14). Pinacol bis(trimethylsilyl)aminoalkylboronate (13) can be easily prepared as shown in FIG. 3. Alternatively, treatment of compound (12) with an alkylamineboronic acid provides compound (15).

In another embodiment, this invention relates to compounds of the general Formula III:

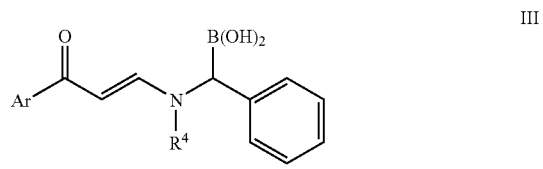

III where Ar is as defined above and $R^4$ is H, an amine protecting group, $Z_n\text{-}OR^1$, $Z_n\text{-}SR^1$, $Z_n\text{-}R^1$, $Z_n\text{-}NR^1(C{=}O)R^1$, $Z_n\text{-}C{=}OR^1$, $Z_n\text{-}OC({=}O)R^1$, $Z_n\text{-}C({=}O)OR^1$, alkyl, allyl, alkenyl, alkynyl, heteroalkyl, heteroallyl, heteroalkenyl, heteroalkynyl, alkoxy, heteroalkoxy, $Z_n$-cycloalkyl, $Z_n$-heterocycloalkyl, $Z_n$-Ar or $Z_n$-heteroaryl, wherein said alkyl, allyl, alkenyl, alkynyl, heteroalkyl, heteroallyl, heteroalkenyl, heteroalkynyl, alkoxy, heteroalkoxy, $Z_n$-cycloalkyl, $Z_n$-heterocycloalkyl, $Z_n$-Ar or $Z_n$-heteroaryl may be substituted or unsubstituted, and where $Z_n$, $R^1$ and n are as defined above.

Figure 4:
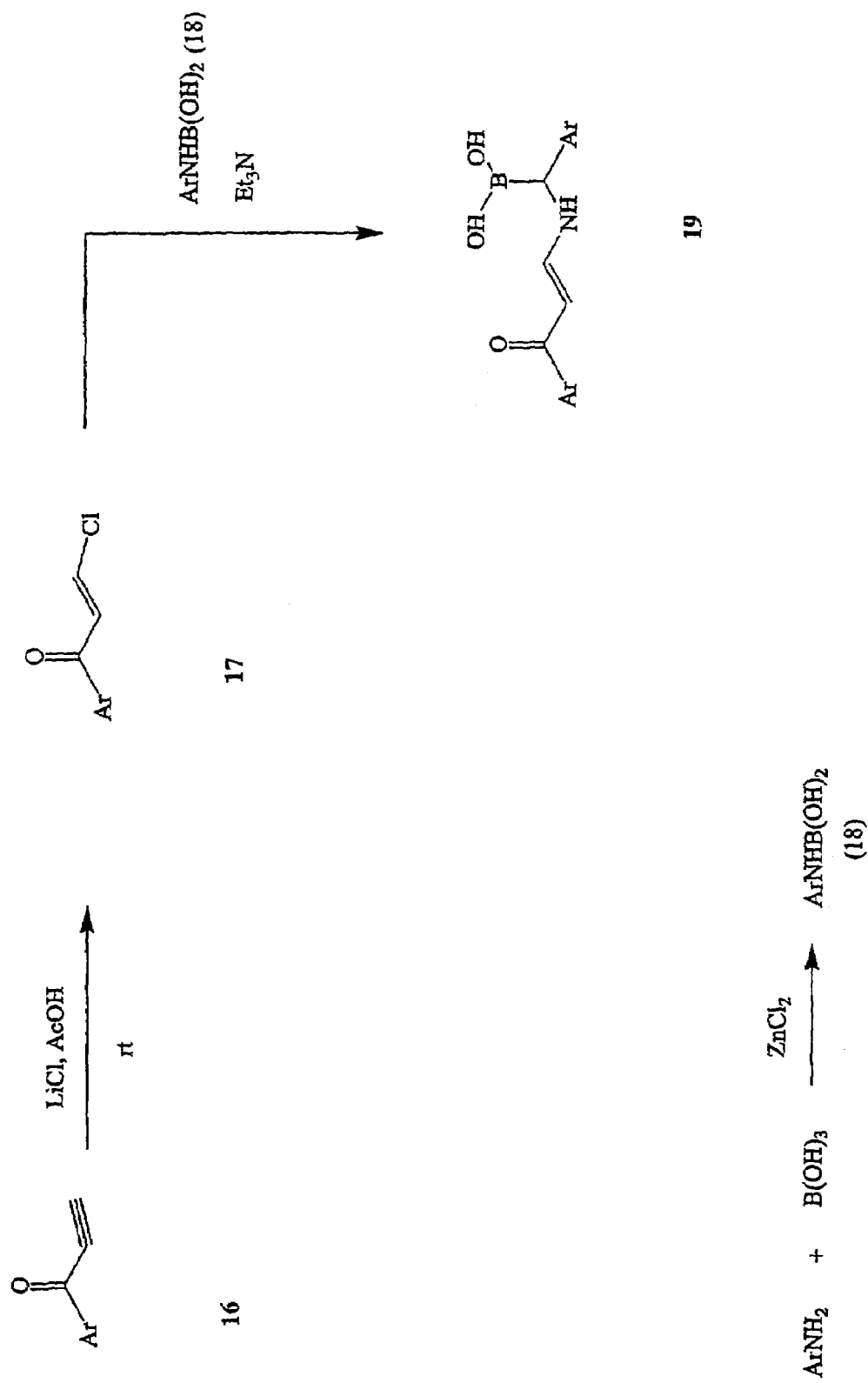
FIG. 4 shows a reaction scheme for the synthesis of compound 19.

FIG. 4 shows a general reaction scheme for the synthesis of chalcone compound (19) based upon structure III. For example, reacting 1-aryl-2-propynon (16) with lithium chloride in acetic acid at room temperature provides 3-chloro-1-arylpropenone (17). Treatment of compound (17) with an arylaminoboronic acid (18) in the presence of triethylamine provides compound (19).

It is important to note that the methods of synthesizing the disclosed compounds are general examples, and one of ordinary skill may readily determine or provide alternative syntheses for producing compounds according to the present invention without engaging in undue experimentation. Using the general and specific synthetic methodologies described herein, a number of the chemical compounds as set forth in Table 1 were synthesized.

The compounds of the present invention are useful for treating or preventing benign and malignant tumors, including various cancers such as, cervical, anal and oral cancers, stomach, colon, bladder, rectal, liver, pancreatic, lung, breast, cervix uteri, corpus uteri, ovary, prostate, testis, renal, brain/cns (e.g., gliomas), head and neck, eye or ocular, throat, skin melanoma, acute lymphocytic leukemia, acute myelogenous leukemia, Ewing's Sarcoma, Kaposi's Sarcoma, basal cell carcinoma and squamous cell carcinoma, small cell lung cancer, mouth/pharynx, esophageal, larynx, kidney and lymphoma, among others. In addition, conditions such as neurofibromatosis, tuberous sclerosis (each of which conditions produces benign tumors of the skin), hemangiomas and lymphangiogenesis, among others, may be treated effectively with compounds according to the present invention.

Methods of treating tumors and/or cancer according to the present invention comprise administering to a patient in need thereof an effective amount of one or more compounds according to the present invention or a pharmaceutically acceptable salt or in vivo cleavable prodrug thereof.

The invention also features methods of combination therapy, such as a method for treating cancer, wherein the above methods further include providing radiation therapy or chemotherapy, for example, with mitotic inhibitors such as a taxane or a vinca alkaloid. Examples of mitotic inhibitors include paclitaxel, docetaxel, vincristine, vinblastine, vinorelbine, and vinflunine. Other therapeutic combinations include a MEK inhibitor of the invention and an anticancer agent such as cisplatin, 5-fluorouracil or 5-fluoro-2-4(1H, 3H)-pyrimidinedione (5FU), flutamide, and gemcitabine. The chemotherapy or radiation therapy may be administered before, concurrently, or after the administration of a disclosed compound according to the needs of the patient.

Numerous biological assays have been used and are accepted by those skilled in the art to assess the anti-tumor and anti-cancer activity of compounds according to the present invention. Any of these methods can be used to evaluate the activity of the compounds disclosed herein. One common method of assessing activity is through the use of test panels of cancer cell lines. These tests evaluate the in vitro anti-cancer activity of particular compounds in cancer cell lines, and provide predictive data with respect to the use of tested compounds in vivo. Other assays include in vivo evaluations of the compound's effect on human or in an appropriate animal model, for example, using mouse tumor cells implanted into or grafted onto mice or in other appropriate animal models.

In the case of testing the anti-cancer activity of compounds according to the present invention, an assay based on human breast cancer MDA-MB-231 (estrogen receptor negative) and wtMCF7 (estrogen receptor positive) cells may be employed as described in Example 2. In this assay, cells are seeded onto a 96-well plate and treated with a compound according to the present invention at a known concentration. The cell numbers are counted and compared against controls. Percent inhibition is readily determined from the data obtained. Other methods known in the art may also be used without undue experimentation to assay the anti-cancer activity of the disclosed compounds.

Therapeutically effective amounts of the compounds of the invention may also be used to treat diseases mediated by expression of MDM2. An "effective amount" is intended to mean that amount of compound that, when administered to a mammal in need of such treatment, is sufficient to inhibit or attenuate expression of MDM2. Thus, for example, a therapeutically effective amount of a compound selected from Formulas I-III, or a salt, active metabolite or prodrug thereof, is a quantity sufficient to modulate, regulate, or inhibit expression of MDM2.

The amount of a given agent that will correspond to such an amount will vary depending upon factors such as the particular compound, disease condition and its severity, the identity (e.g., weight) of the mammal in need of treatment, but can nevertheless be routinely-determined by one skilled in the art. "Treating" is intended to mean at least the mitigation of a disease condition in a mammal, such as a human, and includes, but is not limited to, preventing the disease condition from occurring in a mammal, particularly when the mammal is found to be predisposed to having the disease condition but has not yet been diagnosed as having it; modulating and/or inhibiting the disease condition; and/or alleviating the disease condition.

In order to use a compound of the Formula I-III, or a pharmaceutically acceptable salt or in vivo cleavable prodrug thereof, for the therapeutic treatment (including prophylactic treatment) of mammals including humans, it is normally formulated in accordance with standard pharmaceutical practice as a pharmaceutical composition. According to this aspect of the invention there is provided a pharmaceutical composition that comprises a compound of the Formula I-III, or a pharmaceutically acceptable salt or in vivo cleavable prodrug thereof, as defined hereinbefore in association with a pharmaceutically acceptable diluent or carrier.

The compounds of this invention may be incorporated into formulations for all routes of administration including for example, oral, topical and parenteral including intravenous, intramuscular, eye or ocular, intraperitoneal, intrabuccal, transdermal and in suppository form.

In the pharmaceutical aspect according to the present invention, the compound according to the present invention is formulated preferably in admixture with a pharmaceutically acceptable carrier, excipient or additive. In general, it is preferable to administer the pharmaceutical composition in orally administrable form, but for treatment of a number of conditions, a number of other formulations may be administered via a topical, parenteral, intravenous, intramuscular, transdermal, buccal, subcutaneous, suppository or other route, including an eye or ocular route. Intravenous and intramuscular formulations are preferably administered in sterile saline. Of course, one of ordinary skill in the art may modify the formulations within the teachings of the specification to provide numerous formulations for a particular route of administration without rendering the compositions of the present invention unstable or compromising their therapeutic activity. In particular, the modification of the present compounds to render them more soluble in water or other vehicle; for example, may be easily accomplished by minor modifications (salt formulation, esterification, etc.) which are well within the ordinary skill in the art. It is also well within the skill of those skilled in the art to modify the route of administration and dosage regimen of a particular compound in order to manage the pharmacokinetics of the present compounds for maximum beneficial effect to the patient.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, or intramuscular dosing or as a suppository for rectal dosing). For example, compositions intended for oral use may contain, for example, one or more coloring, sweetening, flavoring and/or preservative agents.

Suitable pharmaceutically-acceptable excipients for a tablet formulation include, for example, inert diluents such as lactose, sodium carbonate, calcium phosphate or calcium carbonate, granulating and disintegrating agents such as corn starch or algenic acid; binding agents such as starch; lubricating agents such as magnesium stearate, stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointestinal tract, or to improve their stability and/or appearance, in either case, using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, or olive oil.

Aqueous suspensions generally contain the active ingredient in finely powdered form together with one or more suspending agents, such as sodium carboxymethylcellulose. methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as ethyl or propyl p-hydroxybenzoate, anti-oxidants (such as ascorbic acid), coloring agents, flavoring agents, and/or sweetening agents (such as sucrose, saccharine, or aspartame).

Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavoring and coloring agents, may also be present.

The pharmaceutical compositions of the invention may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, an esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavoring and preservative agents.

Syrups and elixirs may be formulated with sweetening agents such as glycerol, propylene glycol, sorbitol, aspartame or sucrose, and may also contain a demulcent, preservative, flavoring and/or coloring agent.

The pharmaceutical compositions may also be in the form of a sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent, for example a solution in 1,3-butanediol.

Suppository formulations may be prepared by mixing the active ingredient with a suitable non-irritating excipient which is solid at ordinary temperatures but liquid at the rectal temperature and will therefore melt in the rectum to release the drug. Suitable excipients include, for example, cocoa butter and polyethylene glycols.

Topical formulations, such as creams, ointments, gels and aqueous or oily solutions or suspensions, may generally be obtained by formulating an active ingredient with a conventional, topically acceptable, vehicle or diluent using conventional procedures well known in the art.

Compositions for administration by insufflation may be in the form of a finely divided powder containing particles of average diameter of, for example, 30 µm or much less, the powder itself comprising either active ingredient alone or diluted with one or more physiologically acceptable carriers such as lactose. The powder for insufflation is then conveniently retained in a capsule containing, for example, 1 to 50 mg of active ingredient for use with a turbo-inhaler device, such as is used for insufflation of the known agent sodium cromoglycate.

Compositions for administration by inhalation may be in the form of a conventional pressurized aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

For further information on formulations, see Chapter 25.2 in Volume 5 of Comprehensive Medicinal Chemistry (Corwin Hansch; Chairman of Editorial Board), Pergamon Press 1990, which is specifically incorporated herein by reference.

The amount of a compound of this invention that is combined with one or more excipients to produce a single dosage form will necessarily vary depending upon the host treated and the particular route of administration. For example, a formulation intended for oral administration to humans will may contain, for example, from 0.5 mg to 2 g of active agent compounded with an appropriate and convenient amount of excipients which may vary from about 5 to about 98 percent by weight of the total composition. Dosage unit forms will generally contain about 1 mg to about 500 mg of an active ingredient. For further information on routes of administration and dosage regimes, see Chapter 25.3 in Volume 5 of *Comprehensive Medicinal Chemistry* (Corwin Hansch; Chairman of Editorial Board), Pergamon Press 1990, which is specifically incorporated herein by reference.

The size of the dose for therapeutic or prophylactic purposes of a compound of Formula I-III will naturally vary according to the nature and severity of the conditions, the age and sex of the animal or patient and the route of administration, according to well known principles of medicine.

In one aspect of this invention, the compounds of this invention or pharmaceutical salts or prodrugs thereof may be formulated into pharmaceutical compositions for administration to animals or humans to treat or prevent solid tumors or cancer.

EXAMPLES

In order to illustrate the invention, the following examples are included. However, it is to be understood that these examples do not limit the invention and are only meant to suggest a method of practicing the invention. Persons skilled in the art will recognize that the chemical reactions described may be readily adapted to prepare a number of other boronic chalcones of the invention, and alternative methods for preparing the compounds of this invention are deemed to be within the scope of this invention. For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds of the invention.

In the examples below, unless otherwise indicated all temperatures are set forth in degrees Celsius. Reagents were purchased from commercial suppliers such as Aldrich Chemical Co., Lancaster, TCI or Maybridge, and used without further purification unless otherwise indicated. The reactions set forth below were done generally under a positive pressure of nitrogen or argon or with a drying tube (unless otherwise stated) in anhydrous solvents. The reaction flasks were typically fitted with rubber septa for the introduction of substrates and reagents via syringe. Glassware was oven dried and/or heat dried.

Example 1

General Procedure for the Preparation of Boronic Chalcone Analogs

To a solution of an acetophenone in methanol (10 mL/mmol) was added an aldehyde (1.5 equiv) followed by an aqueous solution of KOH (50%, 1 mL/mmol of acetophenone). The mixture was heated at 70° C. for 4-6 hours and monitored by TLC. Water (20 mL) was then added, the methanol was evaporated, and the solution was extracted with $CH_2Cl_2$. The organic layer was dried and evaporated to dryness, then purified by recrystallization with methanol-water to afford the desired chalcone.

Example 2

Compound 3a $^1$H NMR (400 MHz, $CD_3OD$) δ (ppm): 7.53 (d, J=8.4 Hz, 2H), 7.71 (d, J=16 Hz, 1H), 7.79 (d, J=16 Hz, 1H), 7.82 (m, 4H), 8.05 (d, J=8 Hz, 2H); m.p. 268-270° C.; mass spectrum (EI mode): m/z=377 $[M]^{+\cdot}$ ($^{10}B$), 378 $[M]^{+\cdot}$ ($^{11}B$); Yield 86%.

Example 3

Compound 3b $^1$H NMR (400 MHz, $CD_3OD$) δ (ppm): 7.59 (d, J=8 Hz, 1H), 7.69-7.73 (m, 2H), 7.77 (d, J=8 Hz, 2H), 7.83 (d, J=15.6 Hz, 1H), 7.98 (d, J=2 Hz, 1H), 8.07 (d, J=8 Hz, 2H); m.p. 267-268° C.; mass spectrum (EI mode): m/z=319 $[M]^{+\cdot}$ ($^{35}Cl^{35}Cl^{10}B$), 320 $[M]^{+\cdot}$ ($^{35}Cl^{35}Cl^{11}B$), 321 $[M]^{+\cdot}$ ($^{35}Cl^{37}Cl^{10}B$), 322 $[M]^{+\cdot}$ ($^{35}Cl^{37}Cl^{11}B$), 323 $[M]^{+\cdot}$ ($^{37}Cl^{37}Cl^{10}B$), 324 $[M]^{+\cdot}$ ($^{37}Cl^{37}Cl^{11}B$); Yield 80%.

Example 4

Compound 3c $^1$H NMR (400 MHz, $CD_3OD$) δ (ppm): 7.14 (d, J=8.4 Hz, 1H), 7.66 (d, J=8 Hz, 2H), 7.68 (d, J=15.2 Hz, 1H), 7.72 (d, J=15.2 Hz, 1H), 7.77 (d, J=8.4 Hz, 1H), 7.86 (d, J=2.4 Hz, 1H), 8.05 (d, J=8 Hz, 2H); m.p. 242-243° C.; mass spectrum (EI mode): m/z=303 $[M]^{+\cdot}$ ($^{35}Cl^{10}B$), 304 $[M]^{+\cdot}$ ($^{35}Cl^{11}B$), 305 $[M]^{+\cdot}$ ($^{37}Cl^{10}B$), 306 $[M]^{+\cdot}$ ($^{37}Cl^{11}B$); Yield 90%.

Example 5

Compound 3d $^1$H NMR (400 MHz, $CD_3OD$) δ (ppm): 7.15 (dd, J=8.4 Hz, 8.8 Hz, 1H), 7.61 (m, 2H), 7.51 (m, 1H), 7.63 (d, J=15.6 Hz, 1H), 7.73 (d, J=15.6 Hz, 1H), 7.77 (m, 1H), 8.05 (d, J=7.8 Hz, 2H); m.p. 254-255° C.; mass spectrum (EI mode): m/z=287 $[M]^{+\cdot}$ ($^{10}B$), 288 $[M]^{+\cdot}$ ($^{11}B$); Yield 85%.

Example 6

Compound 3e $^1$H NMR (400 MHz, $CD_3OD$) δ (ppm): 7.12 (d, J=8.4 Hz, 1H), 7.66 (d, J=16 Hz, 1H), 7.71 (d, J=16 Hz, 1H), 7.73 (m, 1H), 7.77 (d, J=8 Hz, 2H), 8.01 (d, J=0.2 Hz, 1H), 8.05 (d, J=8 Hz, 2H); m.p. 163-164° C.; mass spectrum (EI mode): m/z=347 $[M]^{+\cdot}$ ($^{79}Br^{10}B$), 348 $[M]^{+\cdot}$ ($^{79}Br^{11}B$), 349 $[M]^{+\cdot}$ ($^{81}Br^{10}B$), 350 $[M]^{+\cdot}$ ($^{81}Br^{11}B$); Yield 89%.

Example 7

Compound 3f $^1$H NMR (400 MHz, $CD_3OD$) δ (ppm): 4.81 (s, 2H), 7.04 (d, J=8.8 Hz, 2H), 7.62 (d, J=15.6 Hz, 1H), 7.66 (d, J=8 Hz, 2H), 7.8 (d, J=8.4 Hz, 2H), 7.97 (d, J=15.6 Hz, 1H), 8.13 (d, J=8.8 Hz, 2H); m.p. 281-282° C.; mass spectrum (EI mode): m/z=408 $[M]^{+\cdot}$ Yield 90%.

Example 8

Compound 3g $^1$H NMR (400 MHz, $CD_3OD$) δ (ppm): 4.91 (s, 2H), 7.07 (d, J=9.2 Hz, 2H), 7.58 (d, J=8.8 Hz, 1H), 7.67 (m, 2H), 7.82 (d, J=15.6 Hz, 1H), 7.95 (d, J=2 Hz, 1H), 8.12 (d, J=9.2 Hz, 2 H); m.p. 186-187° C.; mass spectrum (EI mode): m/z 350 $[M]^{+\cdot}$ ($^{35}Cl^{35}Cl$) 352 $[M]^{+\cdot}$ ($^{35}Cl^{37}Cl$), 354 $[M]^{+\cdot}$ $^{37}Cl^{37}Cl$); Yield 95%.

Example 9

Compound 6

$^1$H NMR (400 MHz, $CD_3OD$) δ (ppm): 6.93 (d, J=8 Hz, 2H), 7.36 (d, J=8.4 Hz, 2H), 7.52 (d, J=15.6 Hz, 1H), 7.71 (d, J=15.6 Hz, 1H), 7.76 (d, J=8 Hz, 2H), 8.0 (d, J=8.4 Hz, 2H); m.p. 215-216° C.; mass spectrum (EI mode): m/z=350 $[M]^{+\cdot}$ Yield 98%.

Example 10

Compound 7

$^1$H NMR (400 MHz, $CD_3OD$) δ (ppm): 3.41 (s, 2H), 7.01 (d, J=8.8 Hz, 2H), 7.12 (d, J=8.8 Hz, 2H), 7.5 (d, J=8.4 Hz, 2H), 7.65 (d, J=15.6 Hz, 1H), 7.80 (d, J=15.6 Hz, 1H), 8.05 (d, J=8.4 Hz, 2H); mass spectrum (EI mode): m/z=407 [M]+ ($^{10}$B), 408 [M]+ ($^{11}$B); Yield 45%.

Example 11

Compound 8

$^1$H NMR (400 MHz, CD$_3$OD) δ (ppm): 7.67-7.741 (m, 6H), 7.82 (d, J=15.6 Hz, 1H), 7.99 (dd, J=8.2 Hz, 1.6 Hz, 1H), 8.19 (d, J=1.6 Hz, 1H); m.p. 283-285° C.; mass spectrum (EI mode): m/z=319 [M]+ ($^{35}$Cl$^{35}$Cl$^{10}$B), 320 [M]+ ($^{35}$Cl$^{35}$Cl$^{11}$B), 321 [M]+ ($^{35}$Cl$^{37}$Cl$^{10}$B), 322 [M]+ ($^{35}$Cl$^{37}$Cl$^{11}$B), 323 [M]+ ($^{37}$Cl$^{37}$Cl$^{10}$B), 324 [M]+ ($^{37}$Cl$^{37}$Cl$^{11}$B); Yield 68%.

Example 12

Compound 9

$^1$H NMR (400 MHz, CD$_3$OD) δ (ppm): 4.79 (s, 2H), 7.02 (d, J=8.8 Hz, 2H), 7.76 (d, J=15.6 Hz, 1H), 7.83-7.91 (m, 4H), 8.11 (dd, J=8 Hz, 2 Hz, 1H), 8.4 (d, J=2 Hz, 1H); m.p. 209-210° C.; mass spectrum (EI mode): m/z=350 [M]+ ($^{35}$Cl$^{35}$Cl), 352 [M]+ ($^{35}$Cl$^{37}$Cl), 354 [M]+ ($^{37}$Cl$^{37}$Cl); Yield 78%.

Example 13

Compound 11

$^1$H NMR (400 MHz, CD$_3$OD) δ (ppm): 6.31 (dd, J=2.4 Hz, 3.2 Hz, 1H), 7.15 (d, J=2.4 Hz, 1H), 7.25 (d, J=3.2 Hz, 1H), 7.55 (d, J=15.6 Hz, 1H), 7.66 (m, 2H), 7.7 (d, J=15.6 Hz, 1H), 7.79 (m, 2H); m.p. 229-231° C.; mass spectrum (EI mode): m/z=240 [M]+ ($^{10}$B), 241 [M]+ ($^{11}$B); Yield 60%.

TABLE 2

Elemental analytical data of the chalcone analogs

| Compound | Molecular formula | Calculated C | H | N | Found C | H | N |
|---|---|---|---|---|---|---|---|
| 3a | C$_{15}$H$_{12}$BIO$_3$ | 47.67 | 3.20 | — | 47.72 | 3.22 | — |
| 3b | C$_{15}$H$_{11}$BCl$_2$O$_3$ | 56.13 | 3.45 | — | 56.23 | 3.52 | — |
| 3c | C$_{15}$H$_{11}$BClFO$_3$ | 59.16 | 3.64 | — | 59.40 | 3.71 | — |
| 3d | C$_{15}$H$_{11}$BF$_2$O$_3$ | 62.54 | 3.85 | — | 62.42 | 3.92 | — |
| 3e | C$_{15}$H$_{11}$BBrFO$_3$ | 51.63 | 3.18 | — | 51.52 | 3.24 | — |
| 3f | C$_{17}$H$_{13}$IO$_4$ | 50.02 | 3.21 | — | 50.16 | 3.29 | — |
| 3g | C$_{17}$H$_{12}$Cl$_2$O$_4$ | 58.14 | 3.44 | — | 57.98 | 3.50 | — |
| 6 | C$_{15}$H$_{11}$IO$_2$ | 51.45 | 3.17 | — | 51.50 | 3.22 | — |
| 7 | C$_{16}$H$_{14}$BIO$_4$ | 47.10 | 3.46 | — | 47.22 | 3.51 | — |
| 8 | C$_{15}$H$_{11}$BCl$_2$O$_3$ | 56.13 | 3.45 | — | 56.28 | 3.50 | — |
| 9 | C$_{17}$H$_{12}$Cl$_2$O$_4$ | 58.14 | 3.44 | — | 58.22 | 3.42 | — |
| 10 | C$_{13}$H$_{11}$NO | 79.16 | 5.62 | 7.10 | 79.34 | 5.68 | 7.12 |
| 11 | C$_{13}$H$_{12}$BNO$_3$ | 64.77 | 5.02 | 5.81 | 64.86 | 5.10 | 5.89 |

Example 12

Cytotoxicity of Boronic Chalcone Analogs

The cytotoxicity of the boronic chalcone analogs and carboxylic acid chalcones were evaluated and compared by MTT survival assays of human breast cancer MDA-MB-435, MDA-MB-231, Wt-MCF7, and MCF-10A cells treated at different concentrations of the analogs.

Human breast cancer MDA-MB-231 (estrogen independent) and wtMCF7 (estrogen dependent) human breast cancer cells were maintained in DMEM medium supplemented with 5% fetal bovine serum, 2 mM glutamine, and 100 units/mL penicillin/streptomycin. MDA-MB-435 (estrogen independent) human breast cancer cells were maintained in IMEM medium supplemented with 5% fetal bovine serum and 2 mM glutamine. Each cell line used has unique growth characteristics spanning the spectrum of tumor invasiveness, differentiation and estrogen dependence. Normal breast epithelial cell lines, MCF-10A and MCF-12A, were maintained in 5% and 10% horse serum in DMEM:Ham's F12 media, respectively, supplemented with 2 mM glutamine, 100 units/mL penicillin/streptomycin, 0.02 μg/mL EGF, 0.01 mg/mL insulin, and 0.1 μg/mL cholera toxin.

Cells were incubated at 37° C. in a 5% CO$_2$ atmosphere. The MTT colorimetric assay was used to determine growth inhibition (Mosmann, T., *J. Immunol. Methods,* 1983, 65, 55-63). Cells were plated in 96-well plates and allowed to attach for 24 hours. Chalcone derivatives based on compounds 20 and 21 below were dissolved in DMSO at 10 mM concentrations. Cells were expose in quadruplicate well to chalcone concentrations of 0.5-100 μM for 96 hours. After 96 hours the media was aspirated, and 100 μL of 1 mg/mL MTT solution (Sigma Chemical Co.) diluted in serum free media was added to each well. After 4 hours of incubation, the MTT solution was removed and 200 μL of 1:1 (v/v) solution of DMSO:ethanol was added to each well to dissolve formazan crystals. The absorbance at A$_{540nm}$ was determined on a plate reader. IC$_{50}$ values were determined from log plots of percent of control vs. concentration. Each compound was assayed twice in quadruplicate. Analogs 3g and 9 have been previously described (Stoll R., et al., supra; Kussie, P. H., et al., supra) and were included for comparative purposes.

| Compound | A | B | C |
|---|---|---|---|
| 3a | I | H | B(OH)$_2$ |
| 3b | Cl | Cl | B(OH)$_2$ |
| 3c | F | Cl | B(OH)$_2$ |
| 3d | F | F | B(OH)$_2$ |
| 3e | F | Br | B(OH)$_2$ |
| 3f | I | H | OCH$_2$COOH |
| 3g | Cl | Cl | OCH$_2$COOH |
| 6 | I | H | OH |
| 7 | I | H | OCH$_2$B(OH)$_2$ |
| 8 | Cl | Cl | B(OH)$_2$ |
| 9 | Cl | Cl | OCH$_2$COOH |

(Structure 20: B-ring–CH=CH–C(=O)–ring–C; Structure 21: B-ring–C(=O)–CH=CH–ring–C)

IC$_{50}$ values were used to determine growth inhibition in the presence of chalcone derivatives. Of particular interest are compounds able to differentially inhibit growth such that human breast cancer cell lines are inhibited but normal breast epithelial cells are significantly less inhibited.

Compound 3a, 3d, 3e, 7, 8, 10 and 11 are 5-10 fold more toxic to human breast cancer cell lines compared to normal breast epithelial cell lines (Table 1). In the presence of these compounds, cell growth in the human breast cancer cell lines MDA-MB-435, MDA-MB-231, and wt-MCF7 is inhibited, indicated by the range of low $IC_{50}$ values from 3.5 to 23. Cell growth in the normal breast epithelial cell lines MCF-10A and MCF-12A is less inhibited, shown by higher $IC_{50}$ values ranging from 11 to 75.

TABLE 1

Chalcones inhibit growth of human breast cell lines[a]

| Compound | MDA-MB-435 $IC_{50}$ | MDA-MB-231 $IC_{50}$ | Wt-MCF7 $IC_{50}$ | MCF-10A $IC_{50}$ | MCF-12A $IC_{50}$ |
|---|---|---|---|---|---|
| 3a | 10 | 8.8 | 7.0 | 75 | 63 |
| 3b | 3.5 | 9.5 | 5.0 | 18 | 11 |
| 3c | 16 | 8.5 | 6.0 | 25 | 22 |
| 3d | 8.8 | 8.8 | 7.8 | 18 | 39 |
| 3e | 8.8 | 9.5 | 8.5 | 17 | 38 |
| 3f | 18 | 44 | 9 | 44 | 38 |
| 3g | 9 | 9 | 13 | 13 | 15 |
| 6 | 4.5 | 8 | 7 | 15 | 30 |
| 7 | 18 | 11 | 9.5 | 38 | 100 |
| 8 | 4 | 8 | 5.5 | 18 | 15 |
| 9 | 13 | 18 | 15 | 12 | 28 |
| 10 | 15 | 15 | 9 | 63 | 38 |
| 11 | 15 | 23 | 19 | 38 | 60 |

[a]$IC_{50}$ values expressed in μM; see biology section for details of the MTT assay.

The foregoing description is considered as illustrative only of the principles of the invention. Further, since numerous modifications and changes will be readily apparent to those skilled in the art, it is not desired to limit the invention to the exact construction and process shown as described above. Accordingly, all suitable modifications and equivalents may be resorted to falling within the scope of the invention as defined by the claims that follow.

The words "comprise," "comprising," "include," "including," and "includes" when used in this specification and in the following claims are intended to specify the presence of stated features, integers, components, or steps, but they do not preclude the presence or addition of one or more other features, integers, components, steps, or groups thereof.

What is claimed is:

1. A compound of Formula (I):

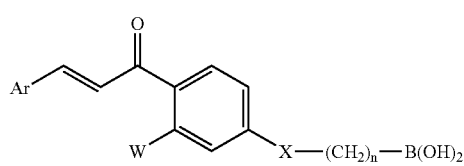

or a pharmaceutically acceptable salt thereof,
where:

Ar is aryl or heteroaryl, each of which may be unsubstituted or substituted with a substituent selected from the group consisting of F, Cl, Br, I, alkyl, allyl, alkenyl, alkynyl, heteroalkyl, heteroallyl, heteroalkenyl, heteroalkynyl, alkoxy, heteroalkoxy, $Z_n$-cycloalkyl, $Z_n$-heterocycloalkyl, $Z_n$-$OR^1$, $Z_n$-$NO_2$, $Z_n$-CN, $Z_n$-$CO_2R^1$, $Z_n$-(C=O)$R^1$, $Z_n$-O(C=O)$R^1$, $Z_n$-O-alkyl, $Z_n$-OAr, $Z_n$-SH, $Z_n$-$SR^1$, $Z_n$-$SOR^1$, $Z_n$-$SO_2R^1$, $Z_n$-S-Ar, $Z_n$-SOAr, $Z_n$-$SO_2$Ar, $Z_n$-Ar, $Z_n$-heteroaryl, $Z_n$-(C=O)$NR^1R^2$, $Z_n$-$NR^1$(C=O)$R^1$, $Z_n$-$SO_2NR^1R^2$, $PO_3H_2$, and $SO_3H_2$;

W is H, $Z_n$-F, $Z_n$-Cl, $Z_n$-Br, $Z_n$-I, $Z_n$-$CF_3$, $Z_n$-$NO_2$, $Z_n$-$OR^1$, $Z_n$-$NR^1R^2$, $Z_n$-$COOR^1$, $Z_n$-$SR^1$, $Z_n$-(C=O)$R^1$, $Z_n$-O(C=O)$R^1$, $Z_n$-$NR^1$(C=O)$R^1$, $Z_n$-(C=O)$NR^1$, alkyl, allyl, alkenyl, alkynyl, heteroalkyl, heteroallyl, heteroalkenyl, heteroalkynyl, alkoxy, heteroalkoxy, $Z_n$-cycloalkyl, $Z_n$-heterocycloalkyl, $Z_n$-Ar or $Z_n$-heteroaryl, wherein said alkyl, allyl, alkenyl, alkynyl, heteroalkyl, heteroallyl, heteroalkenyl, heteroalkynyl, alkoxy, heteroalkoxy, $Z_n$, -cycloalkyl, $Z_n$-heterocycloalkyl, $Z_n$-Ar or $Z_n$-heteroaryl may be substituted or unsubstituted;

X is $Z_n$, $Z_n$-O, $Z_n$-S, $Z_n$-$NR^1$, $Z_n$-$NR^1$(C=O), $Z_n$-C=O, $Z_n$-OC(=O), or $Z_n$-C(=O)O;

$R^1$ and $R^2$ are independently H, an amine protecting group, an alcohol protecting group, an acid protecting group, a sulfur protecting group, alkyl, allyl, alkenyl, alkynyl, heteroalkyl, heteroallyl, heteroalkenyl, heteroalkynyl, alkoxy, heteroalkoxy, $Z_n$-cycloalkyl, $Z_n$-heterocycloalkyl, $Z_n$-Ar or $Z_n$-heteroaryl, wherein said alkyl, allyl, alkenyl, alkynyl, heteroalkyl, heteroallyl, heteroalkenyl, heteroalkynyl, alkoxy, heteroalkoxy, $Z_n$-cycloalkyl, $Z_n$-heterocycloalkyl, $Z_n$-Ar or $Z_n$-heteroaryl may be substituted or unsubstituted, or $R^1$ together with $R^2$ and N forms a saturated or partially unsaturated heterocycle ring having 1 or more heteroatoms in said ring, wherein said heterocycle may be substituted or unsubstituted and wherein said heterocycle may be fused to an aromatic ring;

Z is an alkylene having at least 1 carbon, or an alkenylene or alkynylene each having at least 2 carbons, wherein said alkylene, alkenylene, or alkynylene may be substituted or unsubstituted; and n is zero or any integer.

2. The compound of claim 1 having the structure

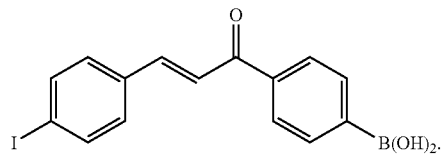

3. The compound of claim 1 having the structure

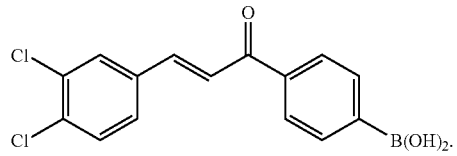

4. The compound of claim 1 having the structure

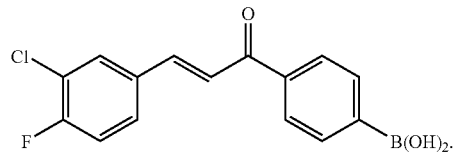

5. The compound of claim 1 having the structure

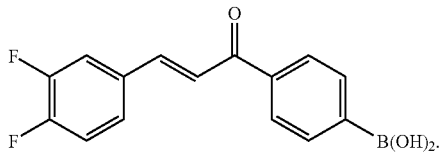

6. The compound of claim 1 having the structure

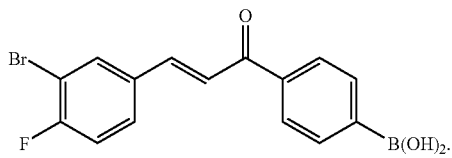

7. The compound of claim 1 having the structure

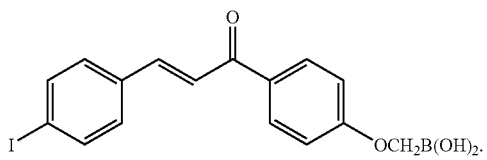

8. The compound of claim 1 having the structure

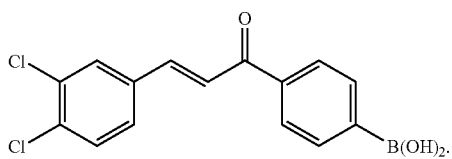

9. The compound of claim 1 having the structure

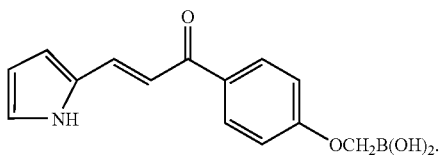

10. A method of treating breast cancer in a patient in need thereof comprising administering to said patient an effective amount of a compound of Formula (I):

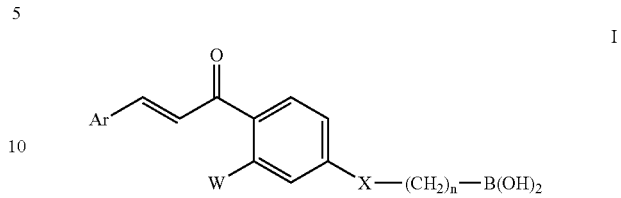

or a pharmaceutically acceptable salt thereof,
where:
Ar is aryl or heteroaryl, each of which may be substituted or unsubstituted;
W is H, $Z_n$-F, $Z_n$-Cl, $Z_n$-Br, $Z_n$-I, $Z_n$-CF$_3$, $Z_n$-NO$_2$, $Z_n$-OR$^1$, $Z_n$-NR$^1$R$^2$, $Z_n$-COOR$^1$, $Z_n$-SR$^1$, $Z_n$-(C=O)R$^1$, $Z_n$-O(C=O)R$^1$, $Z_n$-NR(C=O)R$^1$, $Z_n$-(C=O)NR$^1$, alkyl, allyl, alkenyl, alkynyl, heteroalkyl, heteroallyl, heteroalkenyl, heteroalkynyl, alkoxy, heteroalkoxy, $Z_n$-cycloalkyl, $Z_n$-heterocycloalkyl, $Z_n$-Ar or $Z_n$-heteroaryl, wherein said alkyl, allyl, alkenyl, alkynyl, heteroalkyl, heteroallyl, heteroalkenyl, heteroalkynyl, alkoxy, heteroalkoxy, $Z_n$-cycloalkyl, $Z_n$-heterocycloalkyl, $Z_n$-Ar or $Z_n$-heteroaryl may be substituted or unsubstituted;
X is $Z_n$, $Z_n$-O, $Z_n$-S, $Z_n$-NR$^1$, $Z_n$-NR$^1$(C=O), $Z_n$-C=O, $Z_n$-OC(=O), or $Z_n$-C(=O)O;
R$^1$ and R$^2$ are independently H, an amine protecting group, an alcohol protecting group, an acid protecting group, a sulfur protecting group, alkyl, allyl, alkenyl, alkynyl, heteroalkyl, heteroallyl, heteroalkenyl, heteroalkynyl, alkoxy, heteroalkoxy, $Z_n$-cycloalkyl, $Z_n$-heterocycloalkyl, $Z_n$-Ar or $Z_n$-heteroaryl, wherein said alkyl, allyl, alkenyl, alkynyl, heteroalkyl, heteroallyl, heteroalkenyl, heteroalkynyl, alkoxy, heteroalkoxy, $Z_n$-cycloalkyl, $Z_n$-heterocycloalkyl, $Z_n$-Ar or $Z_n$-heteroaryl may be substituted or unsubstituted, or
R$^1$ together with R$^2$ and N forms a saturated or partially unsaturated heterocycle ring having 1 or more heteroatoms in said ring, wherein said heterocycle may be substituted or unsubstituted and wherein said heterocycle may be fused to an aromatic ring;
Z is an alkylene having at least 1 carbon, or an alkenylene or alkynylene each having at least 2 carbons, wherein said alkylene, alkenylene, or alkynylene may be substituted or unsubstituted; and
n is zero or any integer.

* * * * *